(12) United States Patent
Trice

(10) Patent No.: US 10,433,812 B2
(45) Date of Patent: *Oct. 8, 2019

(54) WIRELESS STETHOSCOPE AND METHOD OF USE THEREOF

(71) Applicant: PULMONARY APPS, LLC, Cleveland, OH (US)

(72) Inventor: Kevin Trice, Cleveland, OH (US)

(73) Assignee: PULMONARY APPS, LLC, Newburgh, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/955,938

(22) Filed: Apr. 18, 2018

(65) Prior Publication Data

US 2018/0279989 A1   Oct. 4, 2018

Related U.S. Application Data

(63) Continuation of application No. 14/575,772, filed on Dec. 18, 2014, now Pat. No. 9,974,515, which is a (Continued)

(51) Int. Cl.
*A61B 7/04* (2006.01)
*A61B 5/00* (2006.01)
(Continued)

(52) U.S. Cl.
CPC ............. *A61B 7/04* (2013.01); *A61B 5/0004* (2013.01); *A61B 5/0022* (2013.01); *A61B 5/024* (2013.01); *A61B 5/02028* (2013.01); *A61B 5/08* (2013.01); *A61B 5/6801* (2013.01); *A61B 5/7203* (2013.01); *A61B 5/7405* (2013.01); *A61B 5/0803* (2013.01); *A61B 5/6833* (2013.01); *A61B 5/6898* (2013.01); *A61B 7/003* (2013.01); *A61B 7/008* (2013.01); *A61B 7/045* (2013.01); (Continued)

(58) Field of Classification Search
CPC .................................. A61B 7/04; A61B 7/045
See application file for complete search history.

(56) References Cited

U.S. PATENT DOCUMENTS

| 2002/0085724 A1 | 7/2002 | Grasfield et al. |
| 2002/0124295 A1 | 9/2002 | Fenwick et al. |

(Continued)

FOREIGN PATENT DOCUMENTS

| CN | 202211702 | 5/2012 |
| EP | 0 959 607 | 11/1999 |

(Continued)

OTHER PUBLICATIONS

File history of U.S. Appl. No. 13/827,443, filed Mar. 14, 2013.
File history of U.S. Appl. No. 14/575,772, filed Dec. 18, 2014.

*Primary Examiner* — Joseph M Dietrich
(74) *Attorney, Agent, or Firm* — Ping Wang; Morris, Manning & Martin, LLP

(57) ABSTRACT

A wireless stethoscope is described, having wireless sensors that are enclosed in disposable pads so that the same pads are not used on more than one patient, preventing cross-infection of patients associated with conventional stethoscopes. The present wireless stethoscope also detects pulmonary sounds and cardiac sounds, allowing the user to monitor one or the other without interference. Also described is a method for diagnosing a pulmonary condition using the wireless stethoscope.

18 Claims, 5 Drawing Sheets

Related U.S. Application Data continuation of application No. 13/827,443, filed on Mar. 14, 2013, now Pat. No. 8,956,305.

(60) Provisional application No. 61/668,191, filed on Jul. 5, 2012.

(51) Int. Cl.
 *A61B 5/02* (2006.01)
 *A61B 5/08* (2006.01)
 *A61B 5/024* (2006.01)
 *A61B 7/00* (2006.01)

(52) U.S. Cl.
 CPC ... *A61B 2562/242* (2013.01); *F04C 2270/041* (2013.01)

(56) References Cited

U.S. PATENT DOCUMENTS

| | | |
|---|---|---|
| 2002/0151812 A1 | 10/2002 | Scheiner et al. |
| 2004/0076303 A1 | 4/2004 | Vyshedskly et al. |
| 2005/0157888 A1 | 7/2005 | Yang |
| 2007/0003072 A1 | 1/2007 | Ward et al. |
| 2007/0106179 A1 | 5/2007 | Bagha et al. |
| 2012/0242501 A1 | 9/2012 | Tran et al. |
| 2014/0270218 A1 | 9/2014 | Wang et al. |

FOREIGN PATENT DOCUMENTS

| | | |
|---|---|---|
| JP | 59-36309 | 3/1984 |
| JP | 61-253046 | 11/1986 |
| JP | 2661124 | 6/1997 |
| JP | 2005-296643 | 10/2005 |
| KR | 20110047181 | 3/2002 |
| KR | 1020050030934 | 3/2005 |
| KR | 1020090070294 | 7/2009 |
| KR | 1020100094042 | 8/2010 |
| KR | 1020100103331 | 9/2010 |
| KR | 1020110047181 | 5/2011 |
| WO | 96/24287 | 8/1996 |
| WO | 0224074 | 3/2002 |
| WO | 2007046504 | 4/2007 |
| WO | 2007149536 | 12/2007 |
| WO | 2008097008 | 8/2008 |
| WO | 2009080040 | 7/2009 |
| WO | 2014167155 | 10/2014 |

WIRELESS STETHOSCOPE AND METHOD OF USE THEREOF

This application is a Continuation of U.S. application Ser. No. 14/575,772, filed Dec. 18, 2014, which is a Continuation of U.S. application Ser. No. 13/827,443, filed Mar. 14, 2013, now U.S. Pat. No. 8,956,305, which claims priority of U.S. Provisional Application No. 61/668,191, filed on Jul. 5, 2012. The entirety of the aforementioned applications is incorporated herein by reference.

FIELD

This application generally relates to medical devices. In particular, the application relates to wireless stethoscopes.

BACKGROUND

Annually, more than one million people contract infections in a hospital while they are being treated for some other disease or condition. One common cause of transfer of infections between patients is the stethoscope. The stethoscope is used on nearly all patients to monitor cardiac, pulmonary or digestive sounds, but is rarely washed between patients. One study sampling 150 stethoscopes found that 133 of them (88%) harbored *Staphylococcus* bacteria. Infections, including nosocomial infections, which are those that are contracted in a medical facility, cost taxpayers over 25 billion dollars annually. While increased washing of stethoscopes or the use of barrier devices, such as plastic sleeves, may reduce nosocomial infections, these options are often not practical in fast-paced medical environments.

Additionally, conventional stethoscopes cannot separate the sounds from one bodily function from another and require the practitioner to listen for pulmonary, cardiac or digestive sounds while the other sounds are also present, and sometimes louder than the sound of interest. While simple non-invasive cardiac function can be monitored by taking a patient's pulse or measuring blood pressure, simple non-invasive pulmonary function can only be adequately determined by directly listening to the lungs with a stethoscope. Placing a hand over the patient's mouth or listening to breath from the mouth and nose do not provide adequate insight into lung function. Furthermore, cardiac and pulmonary sounds tend to be in the same frequency, so pulmonary sounds, particularly weak pulmonary sounds, can be difficult to discern.

Accordingly, there exists a need in the art for a stethoscope device that is useable on a single patient and is disposable in order to prevent transmission of infectious organisms by conventional stethoscopes and for a device that can filter cardiac, pulmonary and digestive sounds, allowing the practitioner to listen to, and focus on, only one type of bodily sound.

As the shortage of medical professionals persists, there exists a need for a stethoscope that will allow for a physician to simultaneously monitor multiple patients.

SUMMARY

One aspect of the present application relates to a wireless stethoscope comprising at least one wireless sensor for monitoring at least one bodily sound and a receiver unit, wherein the wireless sensor detects one or more bodily sounds, converts the one or more bodily sounds into sound signals, and transmits the sound signals wirelessly to the receiver unit, wherein the receiver receives and processes the sound signals and transmits the sound signals to a user-end listening and displaying device.

Another aspect of the present application relates to a wireless stethoscope system, comprising at least one wireless sensor for monitoring at least one bodily sound, a receiver unit and a central transmitting unit, wherein the wireless sensor transmits the at least one bodily sound to the receiver unit by wireless transmission, and wherein the receiver unit is interfaced with the central transmitting unit and further transmits the at least one bodily sound to the central transmitting unit. In some embodiments, the interface between said receiver unit and said central transmitting unit is wired or wireless.

Another aspect of the present application relates to a method for monitoring at least one bodily sound of a patient. The method comprises contacting a wireless sensor with the body of the patient, wherein the wireless sensor detects and wirelessly transmits a bodily sound; receiving the bodily sound with a receiver unit in the vicinity of the patient; wherein the receiver unit is an electronic device selected from the group consisting of cell phones, smart phones, PDAs and tablet computers.

Still another aspect of the present application relates to a method for monitoring at least one bodily sound of a patient. The method comprises contacting a wireless sensor with the body of the patient, wherein the wireless sensor detects and wirelessly transmits a bodily sound; receiving the bodily sound with a receiver unit in the vicinity of the patient; wherein the receiver unit transmits the bodily sound to a listening device, wherein the listening device selected from the group consisting of cell phones, smart phones, PDAs and tablet computers. In some embodiments, the central transmitting unit transmits the bodily sound to an additional listening device. In some embodiments, the additional listening device is selected from the group consisting of cell phones, smart phones, PDAs and tablet computers. In some embodiments, the wireless sensor amplifies detected bodily sound and filters amplified sound to reduce background noise. In other embodiments, the receiver unit filters received bodily sound to reduce back ground noise prior to transmission.

DETAILED DESCRIPTION

Figure 1:
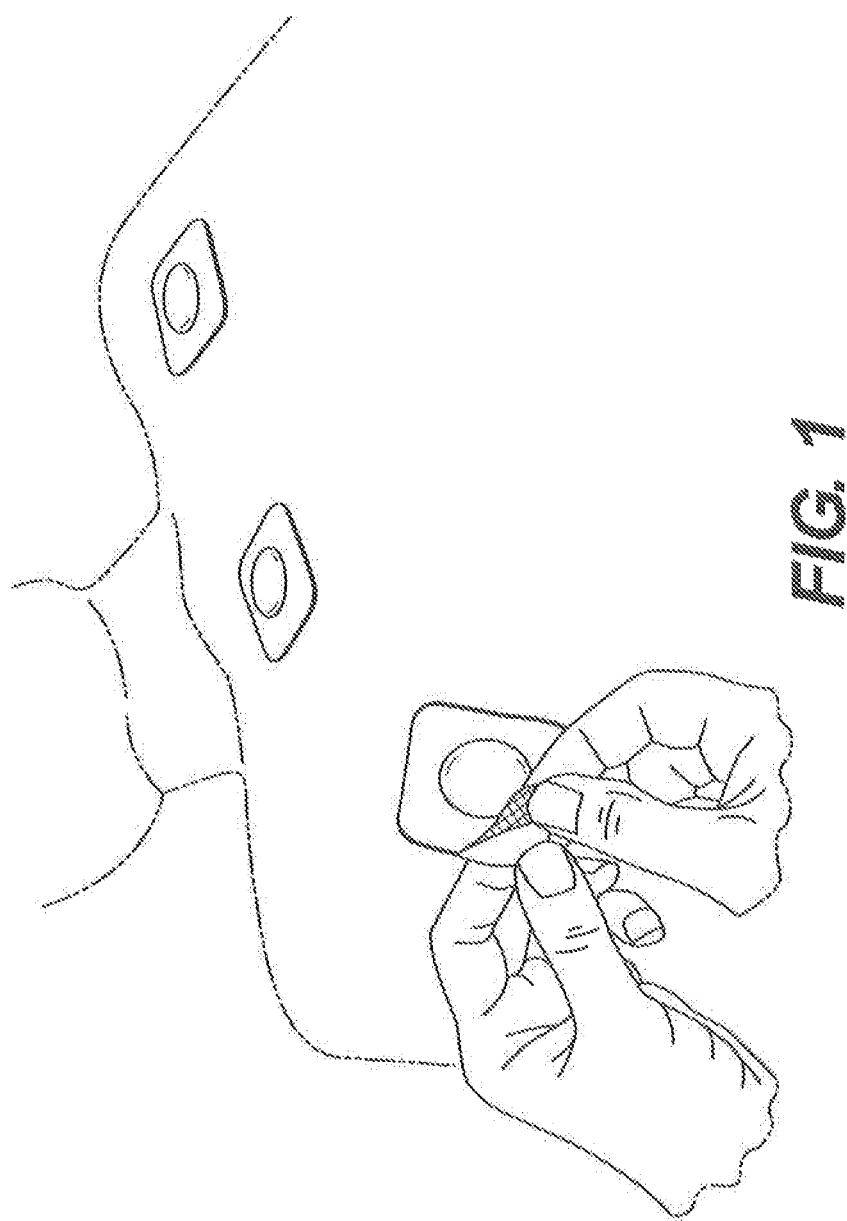
FIG. 1 shows exemplary placement of disposable sensors over the lungs of a patient.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

One aspect of the present application relates to a wireless stethoscope comprising at least one wireless sensor for monitoring at least one bodily sound and a receiver unit, wherein the wireless sensor detects one or more bodily sounds, converts the one or more bodily sounds into sound signals, and transmits the sound signals wirelessly to the receiver unit, wherein the receiver receives and processes the sound signals and transmits the sound signals to a user-end listening and displaying device.

In some embodiments, the wireless sensor is enclosed in or attaches to a disposable pad.

In other embodiments, the wireless sensor comprises at least one microphone that detects bodily sounds.

In other embodiments, the wireless stethoscope comprises more than one wireless sensor programmed to the receiver unit.

In other embodiments, the wireless sensor comprises a rechargeable battery.

In other embodiments, the bodily sound is selected from the group consisting of a pulmonary sound, a cardiac sound, and a digestive sound.

In other embodiments, the receiver unit is an electronic device selected from the group consisting of a cell phone, smart phone, PDA and tablet computer. In other embodiments, the electronic device comprises an application for monitoring said at least one bodily sound.

In other embodiments, the wireless sensor comprises a preamplifier that amplifies bodily sounds within a specific wavelength range.

In other embodiments, the specific wavelength range corresponds to the wavelength of sounds typical of pulmonary sounds or the wavelength of sounds typical of cardiac sounds.

In other embodiments, the wireless sensor comprises a filter circuit that removes or reduces bodily noises that are outside a specific wavelength range. In some embodiments, the specific wavelength range corresponds to the wavelength of sounds typical of pulmonary sounds or the wavelength of sounds typical of cardiac sounds. In some embodiments, the filter circuit further removes or reduces background noises selected from the group consisting of ambient noises, voices, and metallic sounds. In some embodiments, the filter circuit is interfaced with a power amplifier that amplifies bodily sounds that are within the specific wavelength range.

In other embodiments, the wireless sensor comprises an analog to digital converter interfaced to a microcontroller that digitizes bodily sounds that are within the specific wavelength range. In some embodiments, the wireless sensor comprises a transmitter unit for wireless transmission of digitized bodily sounds within a specific wavelength range to the receiver unit. In some embodiments, the wireless transmission is selected from the group consisting of radio frequency communication signals, infrared communication signals, short-wavelength radio transmissions and IEEE 802.15.1 signals.

In other embodiments, the wireless sensor comprises: at least one microphone that detects bodily sounds, a preamplifier that amplifies bodily sounds within a specific wavelength range, a filter that removes or reduces noises that are outside a specific wavelength range, wherein the filter is interfaced with a power amplifier that amplifies bodily sounds that are within said specific wavelength range, an analog to digital converter interfaced to a microcontroller that digitizes bodily sounds that are within said specific wavelength range, and a transmitter unit for wireless transmission of digitized bodily sounds within a specific wavelength range to said receiver unit.

Another aspect of the present application relates to a wireless stethoscope system, comprising at least one wireless sensor for monitoring at least one bodily sound, a receiver unit and a central transmitting unit, wherein the wireless sensor transmits the at least one bodily sound to the receiver unit by wireless transmission, and wherein the receiver unit is interfaced with the central transmitting unit and further transmits the at least one bodily sound to the central transmitting unit. In some embodiments, the interface between said receiver unit and said central transmitting unit is wired or wireless.

In some embodiments, the central transmitting unit is interfaced with more than one receiver unit.

In other embodiments, the central transmitting unit is further interfaced with at least one storage device. In some embodiments, the at least one bodily sound is recorded on the at least one storage device.

In other embodiments, the central transmitting unit is further interfaced with at least one listening device. In some embodiments, the at least one listening device is an electronic device selected from the group consisting of a cell phone, smart phone, PDA, tablet computer and combinations thereof. In some embodiments, the central transmitting unit or said at least one listening device comprises an application that allows a practitioner to monitor at least one bodily sound from more than one patient. In some embodiments, the application analyzes the at least one bodily sound and provides or suggests a preliminary diagnosis based upon the at least one bodily sound.

Another aspect of the present application relates to a method for monitoring at least one bodily sound of a patient. The method comprises contacting a wireless sensor with the body of the patient, wherein the wireless sensor detects and wirelessly transmits a bodily sound; receiving the bodily sound with a receiver unit in the vicinity of the patient; wherein the receiver unit is an electronic device selected from the group consisting of cell phones, smart phones, PDAs and tablet computers.

Another aspect of the present application relates to a method for monitoring at least one bodily sound of a patient. The method comprises contacting a wireless sensor with the body of the patient, wherein the wireless sensor detects and wirelessly transmits a bodily sound; receiving the bodily sound with a receiver unit in the vicinity of the patient; wherein the receiver unit transmits the bodily sound to a listening device, wherein the listening device selected from the group consisting of cell phones, smart phones, PDAs and tablet computers. In some embodiments, the central transmitting unit transmits the bodily sound to an additional listening device. In some embodiments, the additional listening device is selected from the group consisting of cell phones, smart phones, PDAs and tablet computers. In some embodiments, the wireless sensor amplifies detected bodily sound and filters amplified sound to reduce background noise. In other embodiments, the receiver unit filters received bodily sound to reduce back ground noise prior to transmission.

The Wireless Sensor

The wireless sensor comprises at least a detection device that is capable of detecting normal and abnormal bodily sounds, such as normal and abnormal pulmonary sounds, cardiac sounds, digestive sounds, and other bodily sounds. Examples of pulmonary sounds include, but are not limited to, breathing sounds, bronchial sounds, bronchovesicular sounds and vesicular sounds. Examples of abnormal breathing sounds include, but are not limited to, crackles, wheezes, rales, ronchi, stridor and stertor. Examples of abnormal cardiac sounds include, but are not limited to murmurs such as systolic murmurs and diastolic murmurs, abnormal sinus rhythm. Examples of digestive sounds include, but are not limited to, stomach growls, bowel sounds, and borborygmus.

The wireless sensor is capable of picking up a bodily sound, converting the sound into an electrical signal, and transmitting the electrical signal wirelessly to the receiver unit. In some embodiments, the wireless sensor comprises a microphone comprising a transducer that converts a sound into an electrical signal, a printed circuit board (PCB) that processes the electrical signal, and a transmitter that transmits the processed electrical signal wirelessly to the receiver unit. In some embodiments, the wireless sensor simply transmits all the detected sounds to the receiver unit. In other embodiments, the wireless sensor filters the detected sounds to reduce background noise and/or unwanted frequencies, and transmits the filtered sounds to the receiver unit. In other embodiments, the wireless sensor amplifies the detected sounds and transmits the amplified sounds to the receiver unit. In yet other embodiments, the wireless sensor amplifies and filters the detected sounds and transmits the amplified and filtered sounds to the receiver unit.

The microphone can be any microphone suitable to be fitted into a wireless sensor and to pick up a bodily sound. In some embodiments, the microphone is optimized to detect pulmonary sounds. In one embodiment, the microphone is an unidirectional microphone that is sensitive to sounds from only one direction. In other embodiments, the microphone is optimized to detect sound in the frequency range of 20 to 3000 Hz, 20 to 2500 Hz, 20 to 2000 Hz, 20 to 1800 Hz, 20 to 1500 Hz, 20 to 1200 Hz, 20 to 1000 Hz or 20 to 800 Hz In some embodiments, the microphone is a contact microphone that picks up vibrations directly from a solid surface or object, as opposed to sound vibrations carried through air. In one embodiment, the contact microphone comprises a magnetic (moving coil) transducer, contact plate, and contact pin. The contact plate is placed directly on to a body surface, and the contact pin transfers vibrations to the coil.

In some embodiments, the PCB comprises a sound filter circuit that removes or reduces background noise. As used herein, the term "background noise" refers to any noise that is not intended to be captured and transmitted to the receiver unit for monitoring bodily sounds of interest from the subject. For example, background noises include, but are not limited to, ambient sounds, voices, and metallic sounds. In another embodiment, the sound filter circuit is capable of distinguishing cardiac sounds from pulmonary sounds or digestive sounds. In some embodiments, the PCB comprises a filtering circuit for separating cardiac sounds from pulmonary sounds and/or digestive sounds and transmitting only the pulmonary sounds or the cardiac sounds to the receiver. In some embodiments, the PCB comprises an amplification circuit that amplifies the detected bodily sounds or the filtered sounds for transmission. In some other embodiments, the PCB comprises an amplification circuit that selective amplifies the cardiac sounds, the pulmonary sounds, or both cardiac sounds and pulmonary sounds. In some embodiments, the sounds detected by the microphone are amplified first and then filtered to reduce noise and unwanted frequencies. The amplified and filtered sound signals are then digitized for transmission.

The transmitter is capable of transmitting signals wirelessly. In one embodiment, the transmitter transmits signals via radio frequency communication (e.g., a FM radio transmitter). In another embodiment, the transmitter transmits signals via microwave communication. In another embodiment, the transmitter transmits signals via infrared (IR) communication. In some embodiments, the transmitter is a short range transmitter with a maximum transmission range of 50, 25, 10 or 5 feet in order to prevent interference between the signals of wireless stethoscopes used on different patients. In a particular embodiment, the maximum transmission range of the wireless sensor is about 50 feet. In another embodiment, the maximum transmission range of the wireless sensor is about 25 feet. In another embodiment, the maximum transmission range of the wireless sensor is about 10 feet. In yet another embodiment, the maximum transmission range of the wireless sensor is about 5 feet.

In some embodiments, the wireless sensor is capable of converting a detected sound into an electronic sound file and transmitting the sound file instantaneously or within 5, 4, 3, 2 or 1 second from the time of detection.

In other embodiments, the wireless sensor comprise two or more microphones that are capable of picking up different types of bodily sounds. In one embodiment, the wireless sensor comprise two microphones, one is optimized for detecting pulmonary sounds and the other one is optimized for picking up cardiac sounds. In another embodiments, the wireless sensor comprise three microphones, one is optimized for detecting pulmonary sounds, the other one is optimized for detecting cardiac sounds, while the third one is optimized for detecting digestive sounds.

In some embodiments, the wireless sensor is programmable wirelessly through the receiver unit. Examples of the programmable features include, but are not limited to, optimized sounds detection (e.g., pulmonary sounds only, cardiac sounds only, digestive sounds only, or combinations of thereof), transmission range, transmission duration (e.g., 30, 60, 90 or 120 seconds), transmission interval (e.g., every 30, 60, 90 or 120 minutes). In other embodiments, the wireless sensor transmits signal with a unique electronic signature or unique transmission channel so that multiple wireless sensors may be used on a single patient (e.g., at different locations on the patient body) or on different patients (e.g., one or two sensors on each patients) with a single receiver unit. The receiver unit will be able to identify each of the multiple sensors attached to the same patient or each of the multiple sensors attached to different patients based on the unique electronic signature or unique transmission channel of each sensor.

In other embodiments, the wireless sensor further comprises a battery. In a further embodiment, the battery is rechargeable. In another further embodiment, the battery is non-rechargeable. In some embodiments, the wireless sensor has an on/off switch to preserve battery life when the monitor is not in use. In some embodiments, the on/off switch is manually toggled on the wireless sensor. In some embodiments, the on/off switch on the wireless sensor is remotely toggled from a control on the receiver unit or another device. In some embodiments, the wireless sensor is equipped with an Intelligent Power Management system and contains a circuitry that automatically turns off the sensor under pre-set conditions. For example, the on/off switch on the wireless sensor toggles may be automatic when the receiver unit is turned on or off. In some embodiments, there is a removable tab interrupting the current flow from the battery prior to use of the wireless sensor and said tab is removed when the wireless sensor is first used on a patient.

The wireless sensor of the present application is sized for easy attachment to a body part. The wireless sensor can be of any shape or color. In some embodiments, the wireless sensor has a diameter of 5, 4, 3, 2 or 1 cm. In some embodiments, the wireless sensor is a light-weight sensor with a weight of less than 50, 40, 30, 20, 10 or 5 grams. In other embodiments, the wireless sensor is wrapped in a disposable pad. In some embodiments, the disposable pad contains an adhesive to attach the wireless sensor to the body of a patient. In some embodiments, the wireless sensor is a light-weight, short range sensor that has a weight of less than 50, 40, 30, 20, 10 or 5 grams and a transmission range of less than 50, 25, 10 or 5 feet.

In some embodiments, the wireless sensor comprises a disposable pad or cover that is discarded after each use. In other embodiments, the wireless sensor is mountable to a handheld sensor holder.

The Receiver Unit

The receiver unit is capable of receiving a wireless signal from one or more wireless sensors. In some embodiments, the receiver unit receives radio frequency communication signals (e.g., a FM radio signals) from the wireless sensor. In other embodiments, the receiver unit receives microwave or infrared (IR) communication signals from the wireless sensor. In still other embodiments, the receiver unit receives short-wavelength radio transmissions, for example in the ISM band from 2400-2480 MHz (IEEE 802.15.1, or Bluetooth).

In some embodiments, the receiver comprises a filter circuit that reduces the back ground noise in the signals received from the wireless sensor. In some embodiments, the receiver comprises an amplifying circuit and/or an amplifier. In other embodiments, the receiver comprises one or more circuits that filters for, and/or amplifies, desired sounds, such as pulmonary sounds, cardiac sounds, digestive sounds, or combinations thereof.

The receiver can be a single channel receiver or multi-channel receiver. In some embodiments, the receiver is a single channel receiver. In other embodiments, the receiver is a multi-channel receiver that is capable of receiving wireless transmissions from a plurality of wireless sensors. In some embodiments, the receiver is a multi-channel receiver that is capable of programing and/or receiving wireless transmissions from up to 2, 3, 4, 5, 6, 7, 8, 9 and 10 wireless sensors. In some embodiments, the receiver is programmable to designate the multiple channels to two or more patients in a setting where multiple patients are located in the same room. In other embodiments, the receiver is programmable to receiver and/or process only the signals from designated wireless sensors so that two or more receivers can be placed in the same room or in the proximity of each other without interfering with each other.

In some embodiments, the receiver comprises a speaker such that a healthcare professional may listen to the bodily sound transmitted from the wireless sensor. In a related embodiment, the receiver comprises a volume control with or without a mute function. In other embodiments, the receiver does not contain a speaker but can be connected to a speaker to play the sound received from the wireless sensor. In other embodiments, the receiver further comprises a graphic display that is capable of displaying sound waves or sound profiles. In other embodiments, the receiver is a smart phone or tablet.

In some embodiments, the receiver comprises a memory or record means that is capable of storing sound signals received from the wireless sensor. In one embodiment, the receiver stores sound signals received from the last 180, 120, 90, 60, 30 or 10 seconds.

In some embodiments, the receiver is powered by 110 v or 220 v AC power. In other embodiments, the receiver unit is battery powered or comprises a battery back-up. In another embodiment, the wireless sensor further comprises a battery. The battery may be a rechargeable or non-rechargeable battery. In some embodiments, the wireless sensor has an on/off switch to preserve battery life when the monitor is not in use.

In certain embodiments, the receiver further comprises a transmitting unit that is capable of further transmitting the sound files to a user-end unit, such as a central monitoring and/or transmitting unit located at a convenient location such as a nurse station, or a hand-held listening device. The central monitoring/transmitting unit can interface or communicate with multiple receiver units that are each dedicated to wireless sensors attached to different individual patients. The central monitoring/transmitting unit can be interfaced with said multiple receiver units by wired or wireless means or a combination thereof. The central monitoring/transmitting unit can be further interfaced with a computer and/or storage device for processing sounds from the individual patients and/or storing the transmitted bodily sounds from individual patients into a medical record. The central transmitting unit can also interface with the listening device of one or more health practitioners. In some embodiments, the listening device is an electronic device such as, but not limited to, a cell phone, smart phone, PDA or tablet computer. In some embodiments, the central monitoring/transmitting unit is capable of analyzing sounds received from individual patient and providing analysis results that may facilitate diagnosis of the patient.

In some embodiments, the receiver unit simply transmits all the received sounds to the central monitoring/transmitting unit. In other embodiments, the receiver unit filters the received sounds to reduce background noise and/or unwanted frequencies, and transmits the filtered sounds to the central monitoring unit. In other embodiments, the receiver unit amplifies the detected sounds and transmits the amplified sounds to the central monitoring/transmitting unit. In yet other embodiments, the receiver unit amplifies and filters the detected sounds and transmits the amplified and filtered sounds to the central monitoring/transmitting unit.

In some embodiments, the receiver unit, the central monitoring/transmitting unit and/or the end listening devices (such as cell phone, smart phone, PDA or tablet computer) comprises a dedicated software application that allows the health practitioner to, for example, hear the real time bodily sounds transmitted from a patient, delayed bodily sounds transmitted from a patient or previously recorded bodily sounds transmitted from a patient. In some embodiments, the software application provides a visual output representing the real time, delayed, and/or recorded bodily sounds transmitted from a patient. In some embodiments, the software application allows the health practitioner to compare the real time or delayed bodily sounds transmitted from a patient to the delayed or recorded bodily sounds transmitted from said patient. In some embodiments, the software application processes the bodily sounds transmitted from a patient and provides the health practitioner with a preliminary diagnosis of the patient's condition.

Another aspect of the present application relates to a method for monitoring bodily sounds of a patient comprising: programming at least one wireless sensor of a wireless stethoscope to transmit to a receiver unit, contacting said wireless sensor with the body of the patient, and monitoring the bodily sounds detected by the wireless sensor. In a particular embodiment, the bodily sounds are pulmonary sounds. In another particular embodiment, the bodily sounds are cardiac sounds. In another particular embodiment, the bodily sounds are digestive sounds.

In another particular embodiment, the wireless sensor is comprised in a disposable pad. In a further embodiment, the disposable pad is adhered to a single location on the skin of the patient. In another further embodiment, the disposable pad is contained in a handheld sensor holder unit that is movable on the body of the patient.

Figure 3A:
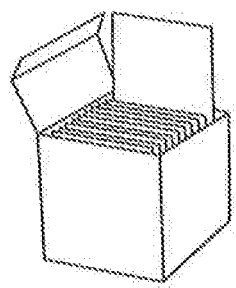
FIGS. 3A-E show an exemplary schematic showing components of the device and their deployment.
Figure 3B:
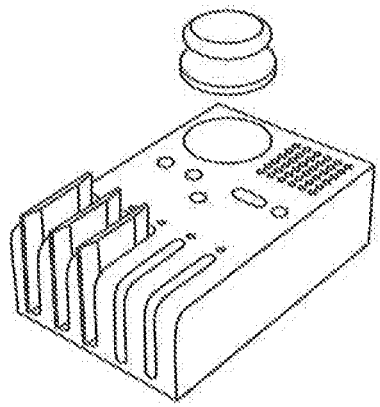
Figure 3C:
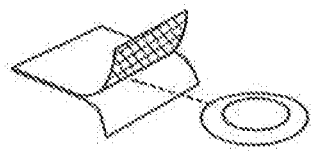
Figure 3D:
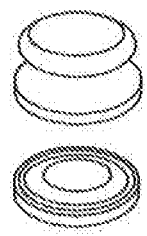

FIG. 1 shows an embodiment of a wireless sensor. In this embodiment, the wireless sensor is enclosed in a disposable pad that makes direct contact with the skin of the patient. Also in this embodiment, the disposable pad has an adhesive surface that is applied to the skin of the patient. In this case, the disposable pad comprising the wireless sensor can remain on the same location of patient during the entire time that monitoring is required, such as during a hospital stay. In other embodiments, the wireless sensor is mounted on a handheld sensor holder as shown, for example, in FIG. 3D. The handheld handle can be used in the same manner as a conventional stethoscope, being moved around to different locations on the patient's body.

Figure 3E:
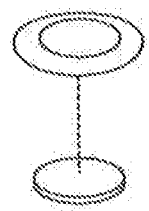

In either case, when there is no longer a need to monitor the bodily sounds of said patient, the disposable pad is discarded. In some embodiments, for example, as shown in FIG. 3E, the wireless sensor is removed from the disposable pad prior to discarding the disposable pad. In some embodiments, the wireless sensor is then sterilized and inserted into a new disposable pad.

Figure 2:
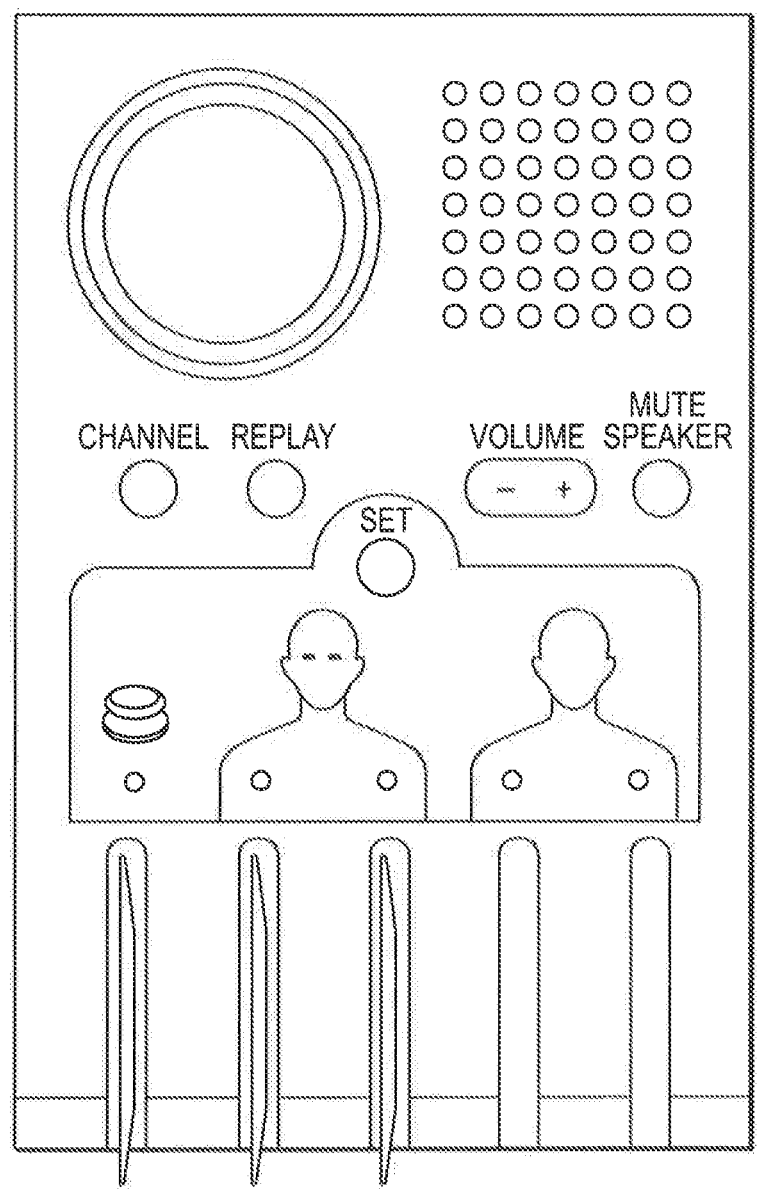
FIG. 2 shows an exemplary receiver unit of the device along with a handheld sensor holder unit, further having ports for the programming of individual sensors.

FIG. 2 shows an embodiment of a receiver unit. The receiver unit is placed in proximity to the patient, in order to receive the signal transmitted by a wireless sensor being used on the patient. In some embodiments, the receiver unit is located at the bedside of the patient. In other embodiments, the receiver unit is worn by the patient, for example when the patient is being transported.

In particular embodiments, the receiver unit is associated with a single wireless sensor being used on a patient. In other embodiments, the receiver unit is associated with multiple wireless sensors. For example, as shown in FIG. 2, a single receiver unit can monitor wireless sensors placed on multiple locations on a patient, such as over each lung on the chest or back, as well as an additional wireless sensor on a handheld sensor holder.

In some embodiments, the receiver unit further comprises a filtering and/or amplifying means for separating cardiac sounds from pulmonary sounds when the wireless sensor transmits both the pulmonary sounds and the cardiac sounds to the receiver unit.

In particular embodiments, as shown in FIG. 2, the receiver unit comprises a speaker for listening to the pulmonary, cardiac or digestive sounds of the patient. In some embodiments, the receiver unit comprises, for example, volume controls, a control for muting the speaker, controls for selecting the wireless sensor being monitored by the receiver unit, controls and contacts, such as a dedicated slot, for programming the association of a wireless sensor with the receiver unit and a place to store a handheld sensor holder unit comprising a wireless sensor associated with the receiver unit.

In some embodiments, the receiver unit comprises a headphone jack so that the practitioner can more closely/clearly hear the pulmonary, cardiac or digestive noises being monitored. In some embodiments, the receiver unit can replay a segment of the monitored noises so that the practitioner can further analyze a noise or event. In a particular embodiment, the receiver unit can replay about the previous 30 seconds of monitored sounds. In another particular embodiment, the receiver unit can replay about the previous 20 seconds of monitored sounds. In still another particular embodiment, the receiver unit can replay about the previous 15 seconds of monitored sounds. In yet another particular embodiment, the receiver unit can replay about the previous 10 seconds of monitored sounds.

FIG. 3 depicts an exemplary programming of wireless sensors to be associated with a particular receive unit. A packaged sterile wireless sensor contained in a disposable pad (FIG. 3A) is contacted with a dedicated slot on a receiver unit (FIG. 3B). The disposable pad comprising a wireless sensor is then removed from the package (FIG. 3C) and placed either in a handheld sensor holder (FIG. 3D) or on the corresponding location (FIG. 2) on the patient's body, as depicted in FIG. 1. When a wireless sensor is no longer needed on the patient, the wireless sensor can either be discarded with the disposable pad, or removed from the disposable pad (FIG. 3E), sterilized and/or refurbished and installed into a new, sterile disposable pad for future reuse.

Figure 4:
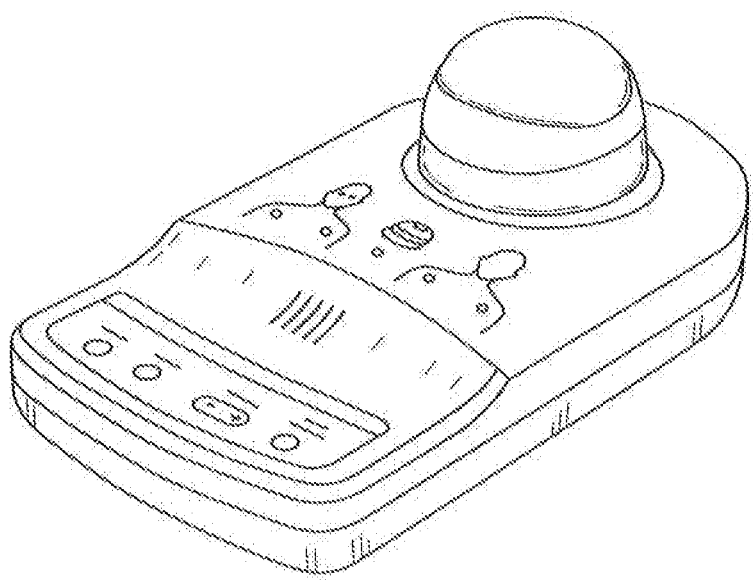
FIG. 4 shows another exemplary receiver unit of the device along with a handheld sensor holder unit.

FIG. 4 depicts another exemplary receiver unit comprising volume controls, a control for muting the speaker, controls for selecting the wireless sensor being monitored by the receiver unit, controls for programming the association of a wireless sensor with the receiver unit and a place to store a handheld sensor holder unit comprising a wireless sensor associated with the receiver unit. In some embodiments, the programming of wireless sensors to be associated with a particular receiver unit is done using a computer, or any other suitable input device, associated with the receiver unit.

In some embodiments, the receiver unit is further connected to a monitoring/transmitting unit. In some embodiments, the connection is a wireless connection. In some embodiments, the connection is a wired or cabled connection. In some embodiments, the monitoring/transmitting unit is, or is further connected to, a computer.

In some embodiments, the monitoring/transmitting unit stores recorded transmissions, or portions thereof, in the medical records of the patient.

Figure 5:
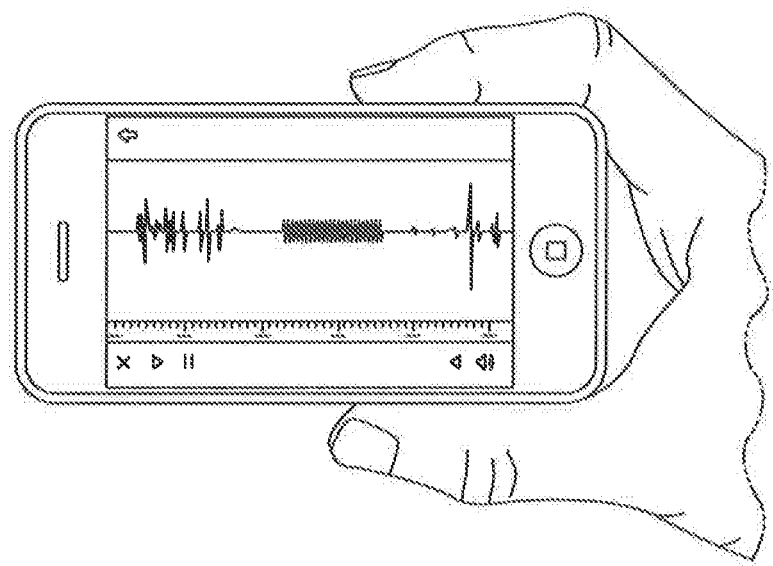
FIG. 5 shows an exemplary graphic of the monitoring of a bodily sound as transmitted to a remote device.

In some embodiments, the monitoring/transmitting unit transmits the bodily sounds detected by the wireless sensor to a user-end listening/displaying device, as shown in FIG. 5, such as, but not limited to, a cell phone, smart phone, PDA or tablet computer. In some embodiments, the sounds are transmitted to the electronic device in real time. In other embodiments, the sounds are transmitted to the electronic device in a delayed transmission. In still other embodiments, the sounds are transmitted to the electronic device as a recording.

In some embodiments, the receiving unit is an electronic device, as shown in FIG. 5, such as, but not limited to, a cell phone, smart phone, PDA or tablet computer. In some embodiments, the electronic device comprises a dedicated software application that allows the health practitioner to, for example, hear the real time bodily sounds transmitted from a patient, delayed bodily sounds transmitted from a patient or previously recorded bodily sounds transmitted from a patient. In some embodiments, the application provides a visual output representing the real time, delayed, and/or recorded bodily sounds transmitted from a patient. In some embodiments, the application allows the health practitioner to compare the real time or delayed bodily sounds transmitted from a patient to the delayed or recorded bodily sounds transmitted from said patient. In some embodiments, the application processes the bodily sounds transmitted from a patient and provides the health practitioner with a preliminary diagnosis of the patient's condition. In other embodiments, the application comprises functionality that allows the health practitioner to listen to, and switch between the bodily sounds from multiple patients. In some embodiments, the application comprises a database of reference sounds that allow the health practitioner to listen to, or see a graphic representation of, an exemplary or representative sound associated with a particular condition.

In some embodiments, the monitoring/transmitting unit transmits the pulmonary, cardiac or digestive sounds detected by the wireless sensor to an electronic device in an audible format. In other embodiments, the monitoring/transmitting unit transmits the pulmonary, cardiac or digestive sounds detected by the wireless sensor to an electronic device as a graphic representation, such as shown in FIG. 5. In still other embodiments, the monitoring/transmitting unit transmits the pulmonary, cardiac or digestive sounds detected by the wireless sensor to an electronic device both in an audible format and as a graphic representation.

In some embodiments, the receiver unit further comprises software that is capable of analyzing the received sound signal and provide a prognosis based on the result of the analysis. In other embodiments, the receiver unit transmits the sound file received from the sensor to a computer having software that is capable of analyzing the received sound signal and provide a prognosis based on the result of the analysis.

Figure 6:
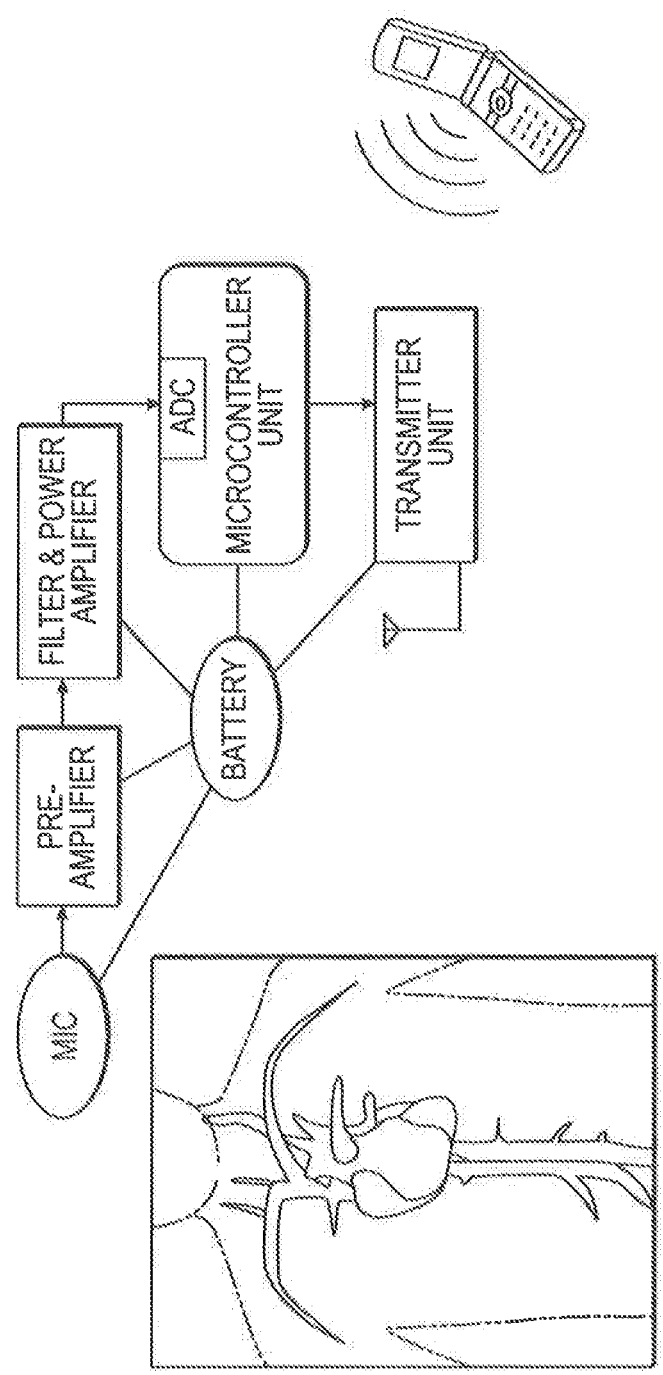
FIG. 6 shows a schematic for an embodiment of the device that can transmit directly to a wirelessly linked listening device.

FIG. 6 shows an embodiment of the device wherein the wireless sensor comprises at least one microphone, at least one preamplifier for cardiac and/or pulmonary sounds, at least one filter unit for removing background noises, at least one power amplifier unit for enhancing auscultation sounds of the desired wavelengths, at least one microcontroller unit for processing and enhancing the sounds to be transmitted and at least one transmission unit that sends the desired sounds wirelessly to a receiver unit. In some embodiments, the wireless sensor further comprises a battery or other power source for powering the microphone(s), preamplifier(s), filter(s), power amplifier(s), microcontroller(s) and transmission unit(s). In some embodiments, the microphone picks up as many bodily sounds as possible and the filter unit is programmed to allow the further transmission of only the bodily sounds that occur within the range of wavelengths of interest.

In some embodiments, the wireless sensor transmits signal directly to a user-end listening or displaying device. In other embodiments, the wireless sensor transmits signal first to a receiver unit. The receiver unit then transmits the signal to a user-end listening or displaying device. In yet other embodiments, the wireless sensor transmits signal first to a receiver unit. The receiver unit transmits the signal to a monitoring/transmitting unit, which then transmits the signal to a user-end listening or displaying device. In the above-described embodiments, the signals may be filtered and/or amplified by the wireless sensor, the receiver unit, the monitoring/transmitting unit, or combinations thereof.

In the case user-end listening or displaying device, the present device comprises wireless connectivity of a monitoring/transmitting unit to a base station. In some embodiments, the wireless connectivity is via Bluetooth. The base station can be a cell phone, smart phone, PDA or a tablet computer. In some embodiments, the smart phone or tablet comprises an installed custom application that will depict the data transferred through the data acquisition device with the ability to review and compare previously recorded data from the patient. The sensor or microphone would detect heart, lung or digestive sounds which would be pre-amplified and filtered for noise and unwanted frequencies prior to digitization. In some embodiments, the microphone would be interfaced to a Analog to Digital Converter (ADC) microcontroller to convert the auscultation sounds to a digital form for transmission. Filtered data could be converted digitally from the microphone by the microcontroller for onward transmission through, for example, a Bluetooth Module in Slave Mode for display and storage. In some embodiments, the wireless module is a battery operated system. In some further embodiments, the battery operated system comprises an intelligent power management (IPM) system. In some embodiments power management is programmable. In some embodiments, the battery is rechargable.

The present application is further illustrated by the following examples which should not be construed as limiting. The present application describes a device with multiple components that have been individually described. It is conceived that these multiple components can be interchanged with one another in any manner that can be imagined by one of skill in the art for the operation of the described wireless stethoscope system. The order in which various components have been described in the present application is not limiting upon the ability to combine said components with one another. The contents of all references, patents and published patent applications cited throughout this application, as well as the Figures and Tables, are incorporated herein by reference.

Example 1: Diagnosis of Pulmonary Condition

A patient presents in the emergency room of a community hospital in pulmonary distress. Disposable tabs comprising wireless sensors are programmed with a receiver unit and placed on the patient's chest and back in the corresponding locations.

The pulmonary sounds that have been detected by the wireless sensors are analyzed by the attending physician. The attending physician consults with a pulmonary specialist in a remote location and transmits audio and graphic representations of the patient's pulmonary sounds to the pulmonary specialist. The attending physician and the pulmonary specialist determine a proper therapeutic course for the patient.

The above description is for the purpose of teaching the person of ordinary skill in the art how to practice the subject of the present application, and it is not intended to detail all those obvious modifications and variations of it which will become apparent to the skilled worker upon reading the description. It is intended, however, that all such obvious modifications and variations be included within the scope of the present application, which is defined by the following embodiments. The embodiments are intended to cover the components and steps in any sequence which is effective to meet the objectives there intended, unless the context specifically indicates the contrary.

What is claimed is:

1. A wireless stethoscope system, comprising:
at least one wireless sensor for monitoring bodily sounds, wherein the at least one wireless sensor comprises a first microphone programmed to detect bodily sounds within a first wavelength range and a second microphone programmed to detect bodily sounds within a second wavelength range,
a receiver unit and a central transmitting unit,
wherein said wireless sensor comprises an analog to digital converter interfaced to a microcontroller that digitizes bodily sounds within said first and second wavelength ranges, wherein said wireless sensor transmits said bodily sounds to said receiver unit by wireless transmission, and wherein said receiver unit is interfaced with said central transmitting unit and further transmits said bodily sounds to said central transmitting unit.

2. The wireless stethoscope system of claim 1, wherein the interface between said receiver unit and said central transmitting unit is wired or wireless.

3. The wireless stethoscope system of claim 1, wherein said central transmitting unit is interfaced with more than one receiver unit.

4. The wireless stethoscope system of claim 1, wherein said central transmitting unit is further interfaced with at least one storage device.

5. The wireless stethoscope system of claim 4, wherein said bodily sounds are recorded on said at least one storage device.

6. The wireless stethoscope system of claim 1, wherein said central transmitting unit is further interfaced with at least one listening device.

7. The wireless stethoscope system of claim 6, wherein said at least one listening device is an electronic device selected from the group consisting of a cell phone, smart phone, PDA, tablet computer and combinations thereof.

8. The wireless stethoscope system of claim 6, wherein said central transmitting unit or said at least one listening device comprises an application that allows a practitioner to monitor said bodily sounds from more than one patient.

9. The wireless stethoscope system of claim 8, wherein said application analyzes said bodily sounds and provides or suggests a preliminary diagnosis based upon said bodily sounds.

10. The wireless stethoscope system of claim 8, wherein said wireless sensor is enclosed in or attaches to a disposable pad.

11. The wireless stethoscope system of claim 8, wherein said wireless stethoscope comprises more than one wireless sensor programmed to said receiver unit.

12. The wireless stethoscope system of claim 8, wherein said wireless sensor comprises a rechargeable battery.

13. The wireless stethoscope system of claim 1, wherein said wireless sensor comprises a preamplifier that amplifies bodily sounds within said first and second wavelength ranges.

14. The wireless stethoscope system of claim 1, wherein said wireless sensor comprises a filter circuit that removes or reduces bodily noises that are outside said first and second wavelength ranges.

15. The wireless stethoscope system of claim 14, wherein said filter circuit further removes or reduces background noises selected from the group consisting of ambient noises, voices and metallic sounds.

16. The wireless stethoscope system of claim 14, wherein said filter circuit is interfaced with a power amplifier that amplifies bodily sounds that are within said first and second wavelength ranges.

17. The wireless stethoscope system of claim 1, wherein said at least one wireless sensor comprises a transmitter unit that transmits said digitized bodily sounds within said first and second wavelength ranges to said receiver unit.

18. The wireless stethoscope system of claim 1, wherein said wireless transmission is selected from the group consisting of radio frequency communication signals, infrared communication signals, short-wavelength radio transmissions and IEEE 802.15.1 signals.

* * * * *